United States Patent
Harp et al.

(10) Patent No.: US 6,315,950 B1
(45) Date of Patent: Nov. 13, 2001

(54) CONTROLLING CHLORINATION OF WASTEWATER AND CHLORAMINATION OF DRINKING WATER

(75) Inventors: Danial L. Harp, Berthoud; Patrick Wiese; Stanley Franklin, both of Loveland, all of CO (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 09/148,716

(22) Filed: Sep. 4, 1998

(51) Int. Cl.$^7$ .................. A01N 2/08; A61L 2/00; A61L 9/00; G01N 33/00

(52) U.S. Cl. .................. 422/28; 436/110; 436/111; 436/125

(58) Field of Search .................. 436/110, 111, 436/125; 422/119, 28, 37

(56) References Cited

U.S. PATENT DOCUMENTS

| | | | |
|---|---|---|---|
| 4,728,498 | * 3/1988 | Theeuwes | 422/29 |
| 5,620,900 | * 4/1997 | Tanzer | 436/113 |
| 5,630,987 | * 5/1997 | Briggs et al. | 422/82 |
| 5,888,758 | * 3/1999 | Wu | 435/28 |

* cited by examiner

Primary Examiner—Terrence R. Till
Assistant Examiner—Monzer R. Chorbaji
(74) Attorney, Agent, or Firm—Dean P. Edmundson

(57) ABSTRACT

A method is described for precisely controlling chlorination of wastewater and chloramination of drinking water. The method involves analyzing the water for the presence of residual monochloramine without interference of dichloramine, organic amines, organic chloramines or nitrites. A color-forming reagent is added to a sample of the water which will develop a colored compound upon reaction with monochloramine, after which the sample may be colorimetrically analyzed to determine the amount of monochloramine present. The method is very accurate and avoids the problems associated with conventional tests used for chlorination control.

7 Claims, 4 Drawing Sheets

ORP PROFILES

CONTROLLING CHLORINATION OF WASTEWATER AND CHLORAMINATION OF DRINKING WATER

FIELD OF THE INVENTION

This invention relates to chlorination of wastewater and chloramination of drinking water. More particularly, this invention relates to processes and techniques for controlling chlorination of wastewater and chloramination of drinking water to maximize the efficiency of disinfection.

BACKGROUND OF THE INVENTION

Traditionally, treated domestic wastewater is disinfected by the addition of chlorine. In recent years, many drinking water facilities have converted to chloramination to disinfect potable water. Chlorine reacts quickly with ammonia (present or added) and any organic nitrogen present in the water to form monochloramine, dichloramine (from ammonia) and organic chloramines (from organic nitrogen compounds). The relative amounts of mono-, di- and organic chloramines formed during the chloramination process depend on the ratio of chlorine-to-nitrogen, pH, temperature, mixing efficiency, and time of contact. Monochloramine and dichloramine (inorganic chloramines) are very effective biocides, but organic chloramines, as a class, have poor disinfection properties.

Monochloramine is the preferred disinfectant for most wastewater treatment facilities that employ biological-oxidation treatment processes (known as secondary treatment). Prior to disinfection, most secondary treatment plants will contain ammonia levels between 0.5–10 mg/L (as nitrogen, N). At pH 7 to 8, and when the mass ratio of chlorine to ammonia-nitrogen is 5:1 or less, all chlorine added is converted to monochloramine. When the applied chlorine (as $Cl_2$) to ammonia-N ratio exceeds 5:1, dichloramine is formed with a corresponding drop in the total biocide concentration (monochloramine+dichloramine, expressed as $Cl_2$). This phenomena is known as breakpoint chlorination and is depicted in FIG. 1.

Although a superior disinfectant, dichloramine formation is usually avoided since more chlorine is unnecessarily consumed and results in a corresponding decrease in total oxidant concentration. Also, the presence of dichloramine can lead to pungent odors in the chlorine contact chambers of some secondary treatment facilities. Dichloramine is not desirable in potable water since its presence can affect both taste and odor.

According to White, "Handbook of Chlorination", Van Nostrand/Reinhold, 3rd Ed., New York, pp. 589–606 (1993), secondary biological wastewater treatment can produce soluble organic nitrogen concentrations in the range of 3–15 mg/L (as N). White also states that if the mixing of chlorine (either gaseous or liquid soda bleach) with the wastewater is poor, the chlorinated species will tend to split between monochloramine and organic chloramines. Several studies have shown that organic chloramines have significantly less germicidal activity than monochloramine.

Other studies, Yoon & Jensen, Water Environ. Res., 67,842 (1995) and Isaac & Morris, Environ. Sci. Technol., 17, 739 (1983), have indicated that, with time, monochloramine can transfer its chlorine to nitrogenous organics, producing the weaker disinfecting organic chloramines. Thus, the germicidal efficiency of chlorinated wastewater has a tendency to decrease with time.

One way to ensure the adequacy of disinfection is to main a total oxidant residual. Thus, one way to control of chlorination is by monitoring the total chlorine residual. This process is known as Chlorine Control by Residual (CCR). In the CCR process, analytical measurements are made either manually (e.g., laboratory or field testing) or automatically (e.g., a process analyzer). All of the commonly used methods of analyses for CCR are based on classical iodometric chemistry. Iodide, added as a reagent, is oxidized by monochloramine, dichloramine and most organic chloramines to the tri-iodide ion:

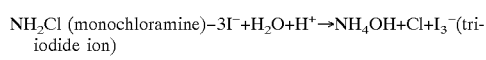

$NH_2Cl$ (monochloramine)$-3I^-+H_2O+H^+ \rightarrow NH_4OH+Cl+I_3^-$ (tri-iodide ion)

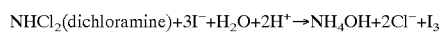

$NHCl_2$(dichloramine)$+3I^-+H_2O+2H^+ \rightarrow NH_4OH+2Cl^-+I_3$

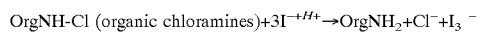

OrgNH-Cl (organic chloramines)$+3I^{-+H+} \rightarrow OrgNH_2+Cl^-+I_3^-$

The resulting tri-iodide, which is formed in direct proportion to the amount of oxidant present, is measured in several ways:

1. Colorimetrically

A reagent indicator, such as N,N diethyl-p-phenylenediamine (DPD) is added and the tri-iodide oxidizes the indicator to a colored form, which can be measured by visual comparison, or suitable instrumentation (e.g., photometer, calorimeter or spectrophotometer). A variation of this technique is colorimetric titration, in which after reaction of the tri-iodide with DPD, the colored product is titrated against a suitable redox titrant, such as ferrous ammonium sulfate, to a colorless end-point.

2. Amperometrically

The tri-iodide ion is sensed by a suitable amperometric system, consisting of a probe or cell containing dual platinum electrodes or two dissimilar electrodes (e.g., silver/platinum) and a voltage generator. A small voltage is applied across the electrodes and the resulting current is compared to a standard reference potential. A variation of this technique is amperometric titration, in which the generated tri-iodide is reacted with a standard reducing titrant, such as phenylarsine oxide or sodium thiosulfate. The current will decrease with decreasing concentration of tri-iodide until no tri-iodide remains. The end-point is signaled when the current does not change. Another variation is known as the back-titration method, in which the released tri-iodide is reacted with an accurate excess amount of standard reductant, such as phenylarsine oxide or sodium thiosulfate. Then, the remaining reductant is titrated with standard iodate-iodide reagent. The end-point can be determined amperometrically or visually using the starch-iodide end-point.

3. Direct Titration with Visual Indication

The generated tri-iodide is titrated against standard thiosulfate titrant to a visual starch-iodide end-point.

The iodometric methods currently used for CCR are not specific for the preferred disinfectant, monochloramine. The CCR-iodometric process will tend to overestimate the disinfection efficiency due to the presence of the poorer disinfecting organic chloramines. Organic chloramines will be present in chlorinated wastewater due to poor mixing, chlorine transfer, or nitrification (which is explained below). Organic chloramines will interfere in all of the common residual analysis methods used for CCR. At the present time, there is no method for CCR based on maintaining a residual specific to the primary preferred disinfectant, monochloramine.

Under certain circumstances, secondary-treated wastewater may nitrify. During nitrification, the ammonia in the wastewater is partially oxidized to nitrite. With low ammonia levels, chlorination of nitrified waters will result in direct chlorination of any organic amines present. Thus, during a nitrifying event, the monochloramine disinfectant level in the chlorinated water may decrease and the organic chloramine level may increase. If nitrification occurs, conventional CCR processes may indicate an adequate disinfection level, when, in fact, disinfection efficiency has diminished.

A second process of controlling chlorination is by use of Oxidation-Reduction Potential (ORP). ORP is based on the concept that it is the oxidative potential derived from the residual that kills the microorganisms and not the concentration of the residual. Instead of maintaining a residual, ORP chlorination control maintains a certain ORP value, measured in millivolts. FIG. 2 shows typical ORP values for different concentrations of monochloramine, dichloramine and a mixture of three organic chloramines. The organic chloramine mixture tested included N-chloro-butylamine, N-chloro-diethylamine and a chlorinated tri-peptide of alanine. This mixture would be representative of organic chloramines found in chlorinated wastewater effluents.

As shown in FIG. 2, ORP can be used to distinguish between pure solutions of dichloramine and monochloramine, but cannot distinguish between monochloramine and any organic chloramines present. Hence, similar to CCR, the weaker disinfecting organic chloramines will also be indicated in ORP chlorination control.

Some wastewater facilities using chlorination find that they have difficulty in meeting their microbial limitations even though residual testing indicates the disinfectant concentration should be sufficient. Likewise, facilities that depend on ORP for chlorination control may experience difficulty in meeting effluent limits for disinfection, although ORP values indicate sufficient oxidation potential. In these cases, both CCR and ORP processes are indicating organic chloramines, which are weak disinfectants. This invention allows accurate chlorination control for the primary disinfectant residual without indicating organic chloramines.

There has not heretofore been described a process for controlling chlorination of wastewater or chloramination of drinking water having the features and advantages provided by the present invention.

SUMMARY OF THE INVENTION

In accordance with the present invention there is provided a process for controlling chlorination of wastewater and chloramination of drinking water. The process involves a method of analysis that is specific for the primary disinfectant, monochloramine. Use of the technique of this invention enables accurate chlorination control for the primary disinfectant residual and is not affected by the presence of organic chloramines, dichloramine, or organic amines.

The process of the invention involves the use of a modification of the Berthelot method of analysis which enables the specific monitoring of residual monochloramine in the chlorine contact chamber. The process ensures that an adequate level of primary disinfectant is available at the outfall of the contact chamber. The process is not affected by nitrites which may be present in the chlorinated water.

Use of the process of this invention enables operators at domestic wastewater facilities to accurately monitor monochloramine disinfectant concentrations and to comply with microbiological limitations permitted for their effluents. It also assists operators in identifying nitrification events while maintaining adequate disinfection. It also aids in the chlorination process used in drinking water treatment to maximize monochloramine formation without production of the dichloramine species. It further allows operators to more efficiently operate their plants by reducing chlorine and ammonia costs.

Other features and advantages of the process of this invention will be apparent from the following detailed description and the accompanying figures.

BRIEF DESCRIPTION OF THE FIGURES

The invention is described in more detail below with reference to the accompanying figures wherein.

DETAILED DESCRIPTION OF THE INVENTION

Figure 1:
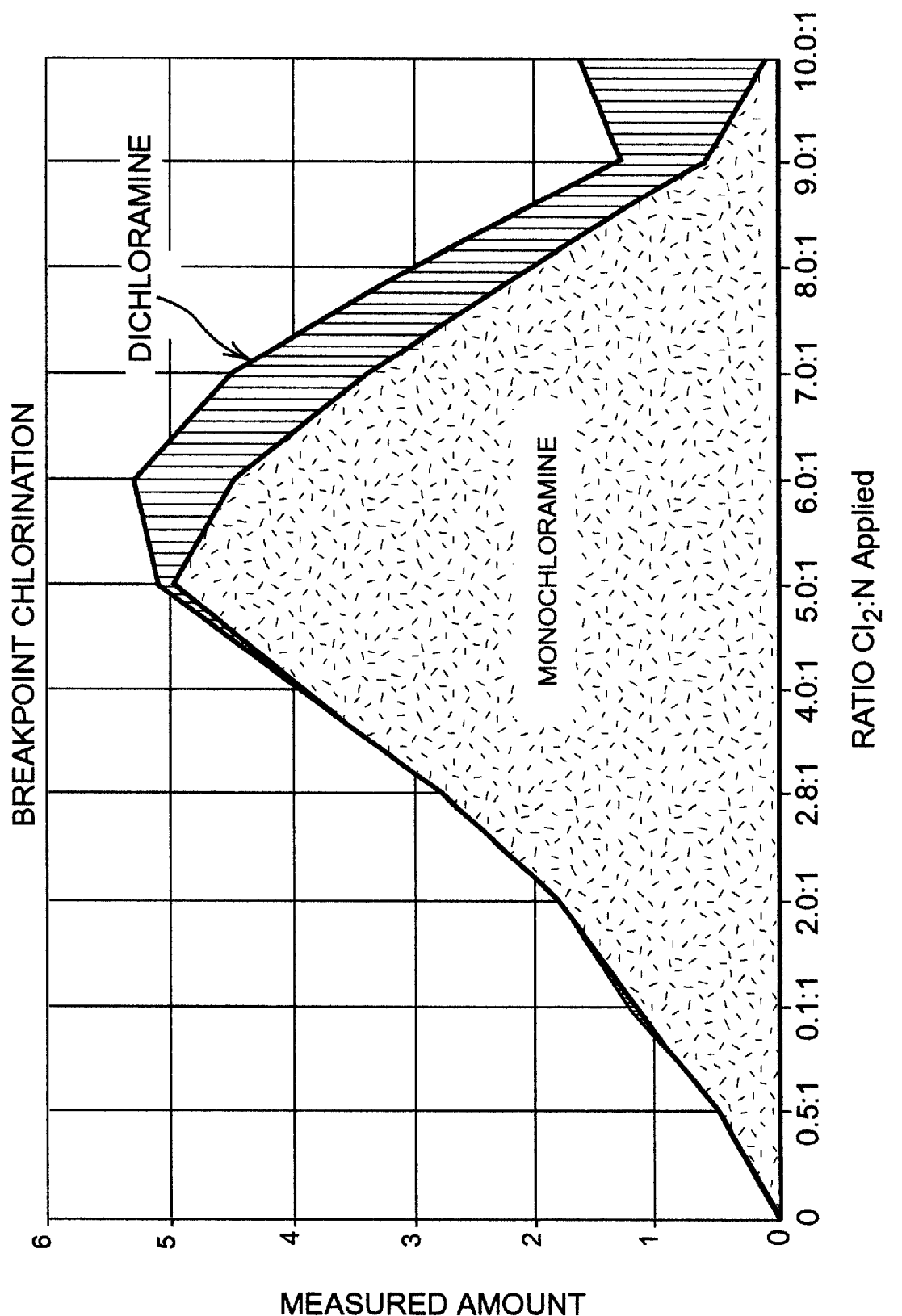
FIG. 1 is a graph illustrating breakpoint chlorination.
Figure 2:
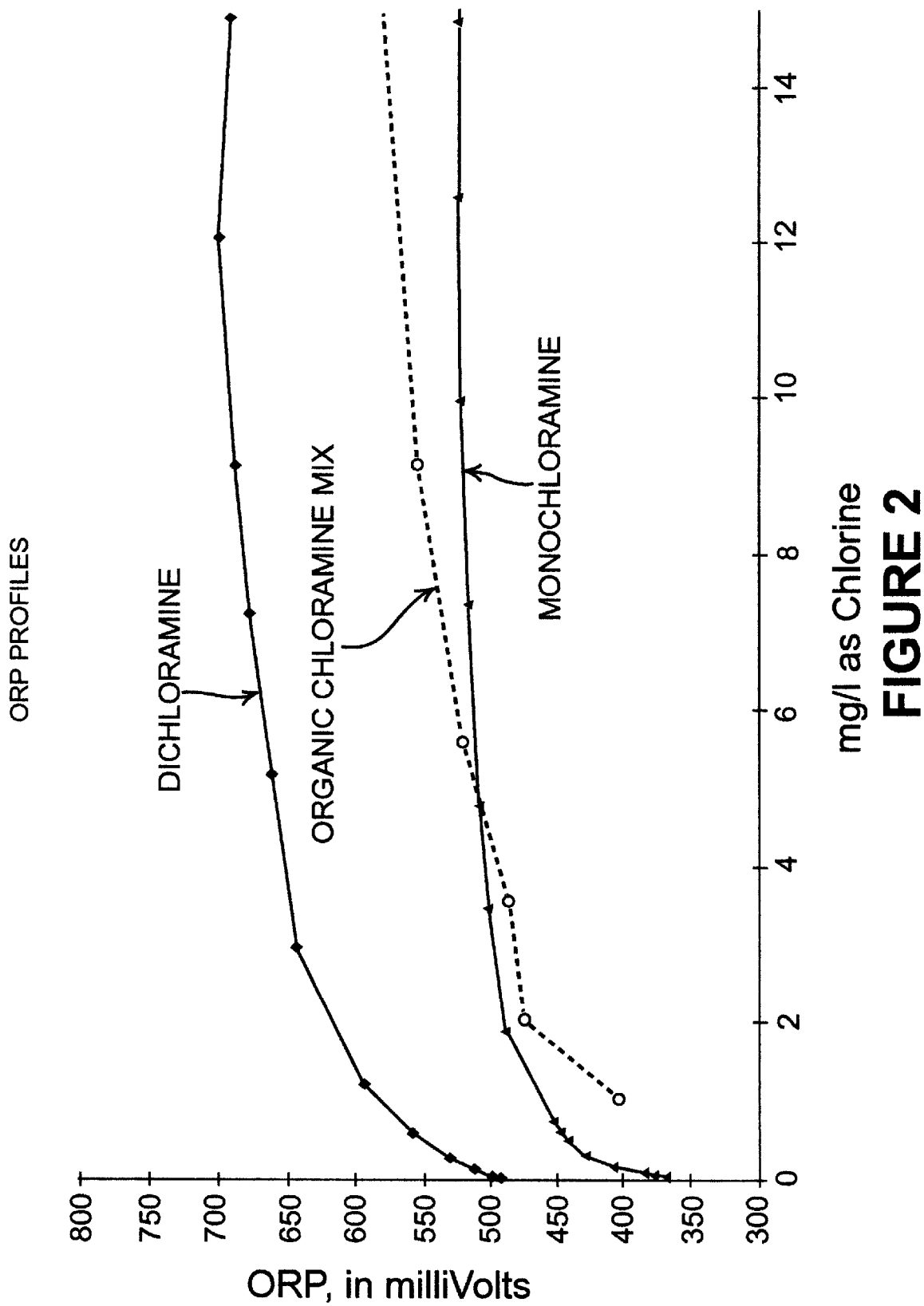
FIG. 2 is a graph illustrating ORP profiles.

The process of the present invention is based on the classical indophenol method for determining ammonia (also known as the Berthelot reactions) in which ammonia, hypochlorite and a phenolic compound combine to form a blue chromophore. The conventional Berthelot reactions are as follows:

1. Monochloramine Formation

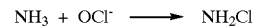

2. Benzoquinone Monoimine Formation

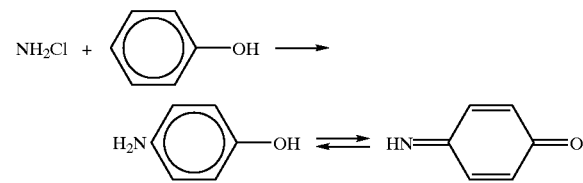

3. Indophenol Formation

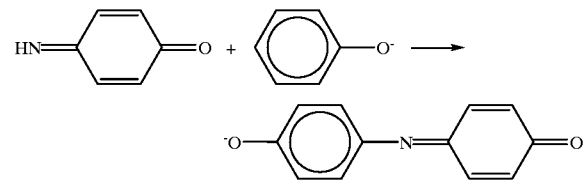

In the present invention, step 1 of the Berthelot sequence of reactions is omitted. It has been established that monochloramine is the reactive intermediate in the Berthelot method, Patton & Crouch, Anal. Chem., 49(3), 464–469 (1977).

Under alkaline conditions and with a catalyst, monochloramine will react with phenol, a substituted phenol or a naphthol to form an indophenolic or indonaphtholic compound which is proportional to the monochloramine concentration. The indophenolic class of compounds can only form if the chloramine has two exchangeable hydrogen atoms. Dichloramines and organic chloramines have no or one exchangeable hydrogen and do not produce indophenol-type compounds under the conditions of the Berthelot reaction.

Hempel and Jensen [*Proceedings of the American Water Works Association Water Quality Technology Conference*, 1990, Part 2, 1033–42] reported using the modified Berthelot reaction in the determination of monochloramine in chlorinated wastewaters. These researchers used phenate reagent with a nitroprusside catalyst at a pH of 10 in an attempt to determine monochloramine in a mixture of a partially chlorinated organic amines. Their conclusions were that although organic chloramines do not appear to positively interfere with the modified Berthelot reaction, there was concern that organic amines and organic chloramines may inhibit the reaction.

In our studies, using the phenate reagents as described by Hempel and Jensen, have demonstrated poor recoveries of inorganic monochloramine in the presence of a mixture of organic amines and organic chloramines (see Table 1, Column A). The mixtures were produced by chlorinating the organic nitrogen substrate at a $Cl_2$:N ratio of 1:3 milligrams per liter (mg/L) at pH 7 and 1 hour in the dark. Under these conditions, it was expected that only organic monochloramines and unchlorinated organic nitrogen substrates would exist. A known amount of inorganic monochloramine was added to the mixture and the amount of monochloramine was determined. As noted in Table 1, using the procedure of Hempel and Jensen, the percent recoveries of inorganic monochloramine in the presence of partially chlorinated organic nitrogen substrates were poor, averaging 34.2%.

Krom [*The Analyst*, Vol. 105, No. 1249, 305 (1980)] reported that the optimum conditions required for the Berthelot reactions is a result of a complex inter-relationship of a number of equilibria and that it is necessary to optimize the pH value for the reagent combinations to be used. Furthermore, he noted that the phenolic compound used must be fully ionized and that a more dilute solution may require a higher pH value to produce a similar concentration of ionized compound. He goes on to state that for any one set of Berthelot reaction conditions, there could be several combinations of experimental conditions that would give similar sensitivity and precision, yet the susceptibility to interference of such variants could differ. Krom's work suggests that the reaction conditions as reported by Hempel and Jensen were not fully optimized for the specific determination of inorganic monochloramine.

Our studies have shown that it is necessary for the ionic strength of the reaction medium and pH to be optimized in order for the modified Berthelot reactions to be specifically applicated for monochloramine. For example, using sodium phenate and nitroprusside as reagents, we found that by adding an ionic compound (e.g. sodium citrate)to increase reaction medium ionic strength and increasing the reaction pH to a value between 12 to 12.5, we can accelerate complete formation of the indophenol product from 60 minutes to less than 20 minutes at room temperature. In addition, the optimized variables using phenate yielded excellent recoveries of inorganic monochloramine in the presence of the partially chlorinated organic nitrogen substrates (see Table 1, Column B).

Ngo, et al., [*Anal. Chem.*, 54, 46–49 (1982)] reported that amines, thiols, and sulfides, at relative high concentrations, can suppress indophenol formation in the determination of ammonia. These researchers postulated that the intermediate benzoquinone monoimine, formed from the reaction of monochloramine and phenol, is especially susceptible to nucleophilic attack by amines and substituted amines. Their proposed mechanism explained that the initial amine attack would occur at the ortho position of the benzoquinone monoimine relative to the oxygen group. Further nucleophilic attack would add a second amino-group ortho to the imino group of the intermediate. The researchers suggested that steric crowding due to the amino additions will inhibit or retard the formation of indophenol.

Examination of the reaction conditions as reported by Ngo, et al., has indicated these may not be optimum, thus allowing for potential interferences in the application of the Berthelot reactions for ammonia determinations. However, if an ortho-substituted phenol (e.g. sodium salicylate) is used in the Berthelot reactions, it is very unlikely that nucleophilic attack of amines on the intermediate benzoquinone monoimine could occur. In the case of salicylate, the presence of the carboxylate group ortho on the phenol will lower the susceptibility of nucleophilic attack on the ring.

Thus, in application of the modified Berthelot reaction for the specific determination of monochloramine, it may be advantageous to use an ortho-substituted phenol to prevent any potential interference from amino compounds. It is important though that the optimum conditions for indophenolic compound formation be established for each substituted phenol employed. Examples of ortho-substituted phenols would include, but are not limited to, salicylate, salicylaldehyde, 2-hydroxy acetophenone, 2-methoxyphenol, o-chlorophenol, 2-hydroxybenzyl alcohol, and o-cresol. Substituted alpha naphthols could also be suitable for monochloramine determination as they will form colored indonaphthol compounds employing the Berthelot reactions.

The preferred catalyst for use in this invention is nitroprusside (sodium or potassium nitroferricyanide) which is commonly used. It has a stabilizing effect on monochloramine at the relatively high pH required for the Berthelot reactions.

Table 1, Column C, shows acceptable recoveries of inorganic monochloramine using salicylate and nitroprusside reagents, under optimum conditions, in the presence of organic amines/organic chloramine mixtures. These data (Columns B & C) proves the specificity of the present invention for the determination of inorganic monochloramine in the presence of organic amines and organic chloramines, typically encountered in chlorinated wastewaters.

In the present invention, with the specificity of the modified Berthelot method, the transfer of chlorine from monochloramine to organic chloramines can be monitored in the chlorine contact chamber. Recent research has shown that monochloramine levels can be reduced by one-half within 70 minutes after formation due to chlorine transfer. Thus, using the modified Berthelot test, an adequate residual of disinfectant can be ensured at the outfall of the chamber.

A CCR process using the modified Berthelot method can help maintain disinfection when the wastestream is nitrifying. During a nitrifying event, the ammonia levels will decrease and monochloramine formation will decrease accordingly. Nitrites and organic chloramines levels, however, will increase. Nitrites, like organic chloramines, can oxidize iodide to the tri-iodide ion and thus will interfere with the common analytical methods for measuring total oxidant concentrations. Since conventional residual control is based on iodometry, the presence of nitrites and organic chloramines may still indicate an adequate level of disinfectant residual when, in fact the active disinfectant concentration has diminished.

Nitrites and organic chloramines do not interfere in the modified Berthelot method. CCR based on the modified Berthelot method of the invention alerts the operators that the active disinfectant level has decreased during nitrification.

In the chloramination process for drinking water, ammonia is added to the treated water in addition to chlorine (as gas or liquid soda bleach). The goal is to optimize formation of monochloramine, without production of dichloramine, and complete reaction of the added ammonia. Organic chloramines can also result from the chlorination of drinking water, although to a lesser extent than in chlorinated treated wastewater. Chloramination control of potable water using the modified Berthelot method optimizes monochloramine formation to a greater extent than the common methods based on iodometry.

The modified Berthelot method is based on colorimetry, and can be tested using existing instrumentation such as calorimeters, photometers, spectrophotometers, or process analyzers. The present invention provides a new residual method for precise chloramination process control suitable for specific monitoring of the primary disinfectant.

The goal of drinking water and wastewater chlorination is disinfection efficiency. This means to achieve adequate and economical disinfection of the microbial population within acceptable limits. Due to the interference of organic chloramines, nitrites and production of undesirable dichloramines, conventional chloramination controls based on iodometry and ORP are inherently less efficient in obtaining disinfection of wastewater. The present invention accomplishes better efficiency in drinking water and wastewater disinfection by chloramination. Residual control using the modified Berthelot method targets the monochloramine residual which provides precise process control. This level of chlorination control has not been previously achievable in wastewater disinfection.

The general procedure for use of the modified Berthelot method for monochloramine determinations pursuant to this invention is described as follows:

1. A suitable volume of water sample is selected for testing. Depending upon the level of expected monochloramine, it may be diluted with low chlorine demand water.
2. A suitable ionic strength adjuster (ISA) is added to the sample or diluted sample and dissolved to maintain a constant and higher ionic strength. An example of one useful ISA is sodium citrate.
3. A suitable amount of nitroprusside (salt of nitroferricyanide) reagent catalyst is added to the sample (or diluted sample) and mixed.
4. A stoichiometric excess of phenol, substituted phenol or naphthol reagent is added to the sample or diluted sample and mixed.
5. The reaction pH is adjusted with a base (e.g. sodium hydroxide) to the optimum pH for indophenol (IP) or indonaphthol (IN) formation. Typical optimum pH values lie between pH 10.5 and 14 depending on the phenol or naphthol selected. Thus, a pH greater than about 10 is preferred.
6. A suitable color development time is allowed for complete IP or IN formation in the sample.
7. The light absorbance of the IP or IN is measured using a suitable calorimeter, photometer or spectrophotometer. Typical absorbance range would be from 600 to 800 nanometers.
8. The sample monochloramine concentration is quantified using a blank and calibration curve generated from monochloramine standards.

It is to be noted that in the foregoing procedure, the reagents, ISA and the base may be combined and dispensed as a powder. Thus, use of a combined reagent system would consolidate steps 2–5 above.

The term "ionic strength" is relative and has its theoretical definition in chemical equilibria and activity. Ionic strength is proportional to (but not equal to) the concentration of electrolytes (acids, bases and salts dissolved in a solution). Representative examples of ISAs which are useful in this invention include inorganic salts (e.g. sodium chloride, sodium sulfate, potassium nitrate, ammonium sulfate, magnesium sulfate, aluminum sulfate and lithium hydroxide), and organic acids and salts (e.g. EDTA and its salts, succinic acid and its salts, citric acid and its salts, and tartaric acid and its salts. Other useful ISAs will be apparent to those of ordinary skill.

The color development time will vary depending upon the particular phenol or naphthol selected, the reaction pH, sample temperature, ionic strength, etc. It may be as short as one minute to as much as 90 minutes, for example. A small increase in temperature can accelerate the reaction.

The invention is further illustrated by means of the following examples.

EXAMPLE 1

A water sample was collected from a secondary-treated sewage treatment facility at a point just prior to chlorination. The sample contained 0.7 mg/L of free ammonia nitrogen.

Small increments of soda bleach were added to the sample and the total residual chlorine was measured at each increment using the conventional DPD-colorimetric method.

Figure 3:
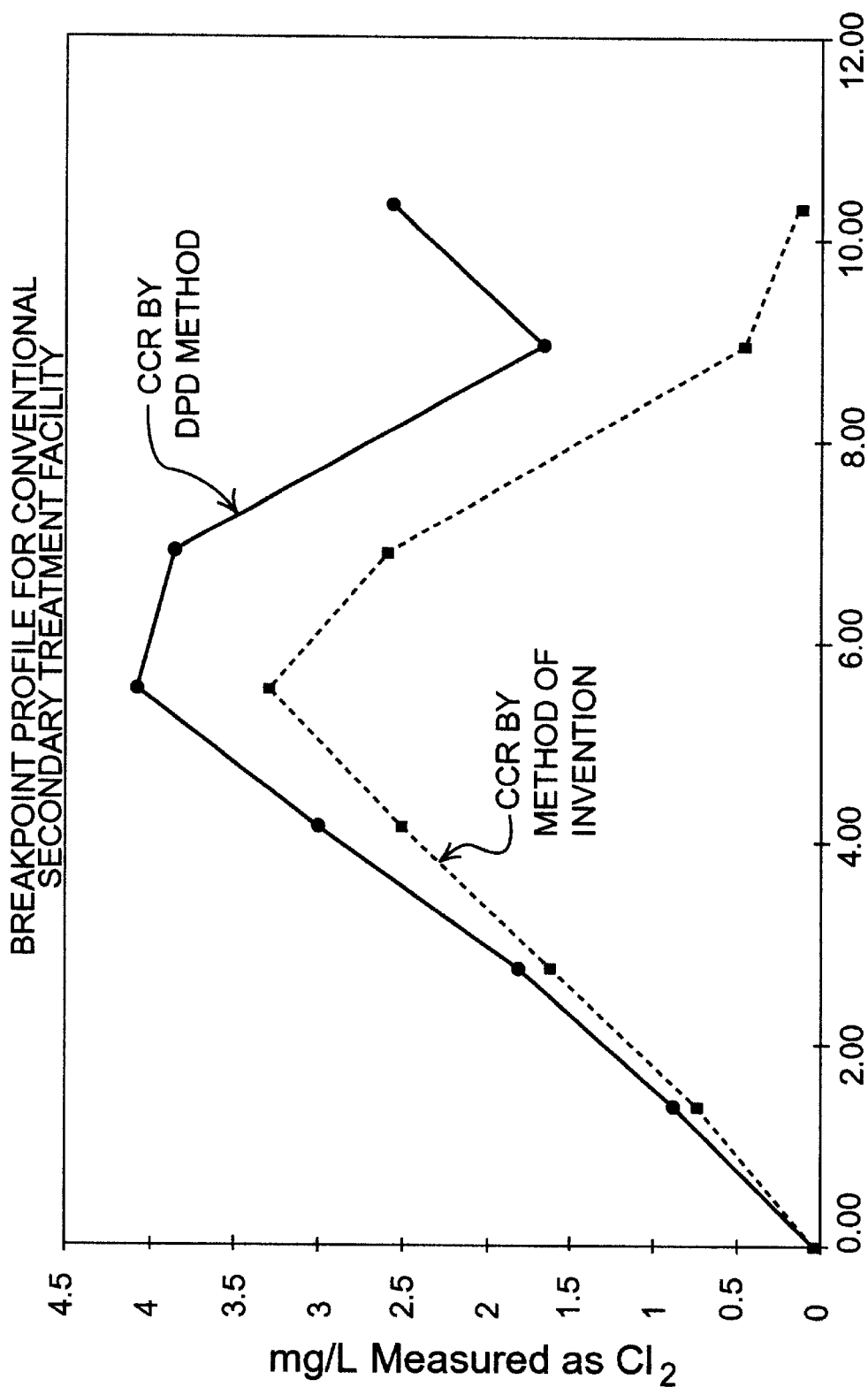
FIG. 3 is a graph illustrating breakpoint profiles for a secondary treatment facility.

Inorganic monochloramine was measured at each increment using the method of the invention as set forth in steps 1–8 above. Increments of chlorine were added through the breakpoint, with the results shown in FIG. 3.

The difference between the DPD and modified Berthelot test of the invention was 0.78 mg/L chlorine at peak monochloramine formation. The conventional DPD method overestimated the disinfection efficiency compared to the method of the invention.

EXAMPLE 2

A water sample was obtained from a hog processing wastewater treatment facility. The facility employed a biological nutrient reduction treatment system to convert much of the nitrogen to nitrates. The treated wastewater is characterized as including high levels of organic N relative to inorganic N.

A sample of treated effluent was collected just prior to disinfection. The ammonia N level in the sample was 0.1 mg/L and the total organic N was 0.8 mg/L.

Figure 4:
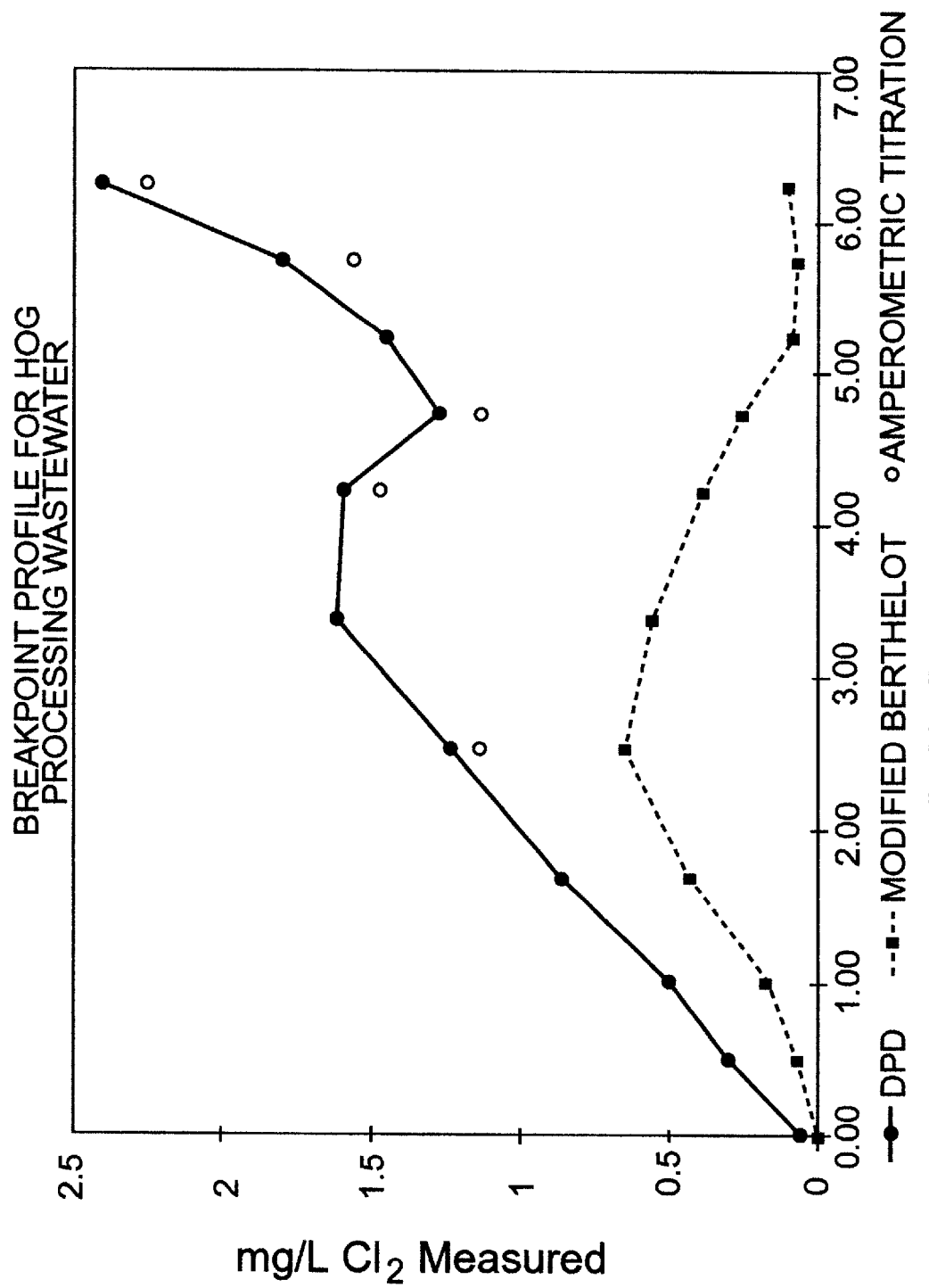
FIG. 4 is a graph illustrating breakpoint profiles for a hog processing wastewater facility.

Small increments of soda bleach were added to the sample. The total residual chlorine was measured by the conventional DPD-colorimetric method and forward amperometric titration method at each increment. Inorganic monochloramine was measured at each increment using the method of the invention as described in steps 1–8 above. Increments of chlorine were added through the breakpoint, with the results being shown in FIG. 4.

The differences between the traditional CCR tests and the modified Berthelot tests of the invention were approximately 1.2 mg/L chlorine at peak monochloramine formation.

The traditional CCR processes will greatly overestimate the disinfection efficiency for this facility due to interference from organic chloramines.

TABLE 1

Recoveries of Monochloramine in Partially
Chlorinated Organic Amine Substrates

| Organic Amine/Chloramine (1:3 $Cl_2$:N) | Column A | Column B | Column C |
|---|---|---|---|
| Alanine | 50.5% | 103.5% | 95.3% |
| Asparagine | 17.2 | 106.5 | 94.4 |
| Diethylamine | 11.5 | 101.7 | 103.6 |
| Glutamic Acid | 29.8 | 102.6 | 91.8 |
| Glycine | 11.8 | 104.5 | 95.9 |
| Tri-Ala-Peptide | 17.5 | 99.7 | 81.0 |
| Tyrosine | 67.5 | 106.6 | 92.8 |
| Urea | 60.5 | 103.5 | 93.5 |
| Average | 34.2% | 103.6% | 93.5% |

What is claimed is:

1. In a method for disinfection of water by contacting the water with chlorine in the presence of ammonia wherein chloramines are formed, the improvement which comprises analyzing said water after addition of said chlorine to determine the concentration of monochloramine in said water without interference of dichloramine or organic chloramines, and comprising the additional steps of (a) adding an additional amount of chlorine to said water, and (b) analyzing said water after said additional amount of chlorine has been added to determine the concentration of monochloramine without interference of of dichloramine or organic chloramines; wherein said steps (a) and (b) are repeated until the concentration of monochloramine in said water is sufficient to provide adequate disinfection of said water.

2. A method in accordance with claim 1, wherein said water comprises wastewater.

3. A method in accordance with claim 1, wherein said water comprises drinking water.

4. A method in accordance with claim 1, wherein said water is analyzed under alkaline conditions by adding a phenol, substituted phenol or a naphthol reagent and a catalyst capable of reacting with monochloramine to form an indophenolic or indonaphtholic compound which is proportional to the amount of monochloramine present.

5. A method in accordance with claim 4, wherein said phenol is selected from the group consisting of sodium salicylate, salicylic acid, 2-hydroxybenzyl alcohol, and 3-hydroxybenzyl alcohol.

6. A method in accordance with claim 4, wherein said naphthol is selected from the group consisting of alpha-naphthol, 1-naphthol-2-sulfonic acid, 1-hydroxy-2-naphthoic acid.

7. A method for disinfection of water in the presence of ammonia by forming monochloramine in said water, and avoiding production of dichloramine and organic chloramines, the method comprising the steps of:

(a) contacting said water with chlorine, wherein the mass ratio of chlorine to ammonia nitrogen is less than about 5:1, whereby monochloramine is formed;

(b) analyzing said water to determine the concentration of said monochloramine in said water without interference of dichloramine or organic chloramines; and (c) repeating steps (a) and (b) until the concentration of monochloramine in said water is sufficient to disinfect said water.

* * * * *